US00PP09339P

United States Patent [19]

Scanvini

[11] Patent Number: Plant 9,339

[45] Date of Patent: Oct. 24, 1995

[54] PEACH TREE 'DUCHESSA D'ESTE'

[76] Inventor: Giorgio Scanvini, Via Bologna, 254, 44100 Ferrara, Italy

[21] Appl. No.: 240,154

[22] Filed: May 10, 1994

[51] Int. Cl.[6] ..... A01H 5/00

[52] U.S. Cl. ..... Plt./42.1

[58] Field of Search ..... Plt./42.1

[56] References Cited

U.S. PATENT DOCUMENTS

P.P. 8,003 10/1992 Zaiger et al. ..... Plt./42.1
P.P. 8,439 10/1993 Zaiger et al. ..... Plt./42.1

*Primary Examiner*—James R. Feyrer
*Attorney, Agent, or Firm*—Jacobson, Price, Holman & Stern

[57] ABSTRACT

A peach tree of large size, medium to slightly above medium vigor, having an ascending to spreading growth habit. Fruit has white flesh and medium to large size. The flesh is sweet and has a pronounced, pleasant flavor, high juice and sugar content, and red striations near the stone cavity. Fruit skin has a heavy red blush over sun exposed surfaces and a lighter pink blush over shaded surfaces over light green-yellow ground color. Fruit is tenaciously attached to the tree and may be harvested over an extended period of time from about August 25 to September 15, depending on growing season. Fruit skin is smooth and blemish free; having a high resistance to cryptogramic diseases. Freestone fruit has uncommonly rounded, symmetrical shape, light tomentum; and, excellent shipping and storage qualities due to its firm, non-melting flesh.

4 Drawing Sheets

BACKGROUND OF THE VARIETY

The present variety is a new white peach variety *Prunus persica* originated in Ferrara, Italy, Po Valley. Applicant is not aware of a similar variety.

ORIGIN OF THE VARIETY

The tree of this discovery was found as a chance seedling originating on my farm in Ferrara, Italy. The seedling was discovered near a specimen of the apparent seed parent, an early ripening variety named 'Fior di maggio'. This tree was planted within pollination distance of a specimen of a compatible pollen variety named 'Amsdem' and is believed to be a hybrid of he two trees. A number of such seedlings were allowed to mature and developed into trees which showed a wide range of characteristics. Upon recognition of the unusual and highly desirable combination of characteristics exhibited by this tree, I took steps to preserve and multiply it for further observation and testing. I collected budwood from this outstanding tree which I budded onto the rootstock variety 'Franco' at the same location. These acts resulted in a number of specimens now being maintained in my orchard which possess the distinctive characteristics of the original selection, to establish that the tree of this invention is stable.

SUMMARY OF THE VARIETY

The new peach tree of this invention has been denominated 'Duchessa D'Este'. It is characterized by bearing attractive, nearly perfectly rounded, smooth, globose fruit of uniform attractive shape, which can be harvested over an extended period between about the last week in August to about the middle of September, with an extensive red blush over a light green-yellow ground color. The fruit has white flesh with a reddish stone or pit cavity surface. The tree may be broadly characterized as being of medium size and as having medium vigor and as being a late ripening variety which tenaciously retains its fruit until it is harvested. Fruit size is uniform throughout the tree and of medium to large size. Peaches ripen to a very high level of sweetness and have a strong, pleasant flavor, a heavy aroma which is wild in character and abundant juice. Further, the fruit is sufficiently firm and dense as to be exceptionally bruise resistant. The surfaces of the fruit which are exposed to light take on an attractive and appealing bright red blush on exposed fruit surfaces, fruit quality can be even further enhanced by prudent pruning and/or training to ensure maximum fruit skin exposure to sunlight.

BRIEF DESCRIPTION OF THE DRAWINGS

A first sheet of the drawings shows, at the top left, a fruit in side elevation with the suture facing forward, at the top right, the internal flesh characteristics and pit of a specimen of the fruit split on the suture line is depicted and at the bottom left and right respectively, the blossom and stem ends of further specimens of the fruit are illustrated;

A second sheet of the drawings depicts the tops of flowers of different maturity on the top left and the bottom of an open blossom on the top right showing the dark anthocyanin color of the sepals; a bisected flower showing the calyx and reproductive organs on the bottom left; and typical detached petals from the flowers on this tree on the bottom right;

A third sheet of the drawings shows two typical leaves from the tree with a ruler to reflect the scale and relative sizes of the leaves, leaf shape and it also shows the characteristics of margin and venation, leaf stem and leaf stem glands in detail; and A fourth sheet of drawings illustrates a bearing twig on the tree having 5 ripe fruit in different orientations along the stem to depict the normal overcoloring, attractive shape and fine tomentum of the fruit as they approach ripeness.

DESCRIPTION OF THE VARIETY

The present invention is of the variety as grown in the Po Valley in Ferrara, Italy. The peach tree and its fruits may vary in slight detail due to climatic and soil condition under which the variety may be grown. The botanical details are as follows:

TREE

Size: Large.
Growth: Medium rising.
Shape: Between ascending and spreading.
Bark coloration and texture: Pale brown (199A) — smooth.
Height and breadth of a mature specimen: 5 mt. (free without pruning).
Density of the branching and canopy: Moderately dense — irregular palmette or spreading with 4 branch.
Internode length: 2 cm.
Angles of the major scaffold branches: 45° (for the plant not>3 mt. Plants>3 mt. not observed.)
Branch/twig strength: strong, no supplemental support needed for heavy crop load.
Layout of planting: Mt. 5×3 or 5×4 depending on the pruning form,
Vigor: Medium — a young bearing specimen will typically attain about one meter of terminal growth.
Lenticels density: Medium.
Lenticels size: Medium.

LEAVES

Average length: 172.4 mm.
Average width: 3.54.
Margin: Crenate.
Petiole: Length 10.2 mm.
Glands: number/2, kidney shaped, located on the basal margin of the leaf.
Stipules: Not observed.

FLOWERS

Flowering shoot: Strong anthocyanic coloration.
Time of beginning flowering: Medium early, March20–April 10 depending on the climatic conditions, generally within March.
Flower shape: Campanulate.
Flower diameter: Cm. 2.5/3.
Petal shape: Elongated.
Petal size; Small — length cm. 1.3/1.5–breadth 0.3/0.4 cm.
Petal color: Dark pink (57B to 57C), white ground color with a pink blush most intensive near the margins and along the veins with the petal central portion and the claws being nearly white.
Petal number: 5.
Pollen color: Yellow bright (15B).
Pollen amount: Abundant.
Timing of pollen release: End of March–beginning of April, just before the end of the flowering.
Self fertility: Yes.

FRUIT

Size: Large — diameter: Medium large, 7 cm. plus.
Weight: 196 grams.
Shape: Nearly symmetrical uniformly rounded.
Apex form: The pistil joint is exceedingly small and normally subtends the smooth curvature of the cheeks, allowing for safer handling and storage with less damage to the fruit.
Suture: Slight indentation, sometimes deep red.
Cavity: Medium depth.
Stone cavity color: White with dark pink veins.
Propensity to split: Yes.
Skin: Smooth.
Tomentum: Very fine and moderately dense.
Ground color: Yellow green (1D).
Anthocyanic coloration: Pink on almost all over the fruit surface (53B–53C), invitingly colored, unusually clear of blemishes for an early to mid late season.
Thickness: Medium.
Adherence to the flesh: Medium.
Tendency to crack: None.
Flesh color: White (158C) with red striations at the stone (46A).
Texture: Medium strong, firm but not crisp, non-melting character.
Juice: Abundant. Flesh fibers are numerous, small and tender and are revealed as minute, visible dots which intersect the slices of cut fruit. A few fibers adhere to the stone when fruit is split.
Anthocyanic coloration under the skin: Slightly present.
Anthocyanic coloration of the flesh: Present.
Anthocyanic coloration around the stone: Present.
Sugar amount of ripe fruit: High level.
Flavor: Excellent — very sweet.
Aroma: Wild.
Amygdalin amount: Absence.
Harvesting period: Normally between the dates of from about August 25 to about September 15, but can vary somewhat due to vagaries in growing seasons from one year to the next. The tree mauy be visited and harvested at any time during the extended ripening period to select fruit at the peak of ripeness which will command the highest price in fresh local markets.
Stone size: Medium.
Length: About 4 to 4.5 cm.
Breadth: About 3 to 3.5 cm.
Width: About 2 to 2.3 cm.
Type: Freestone.
Form: Elliptical.
Color: Pale brown (166B to 166C).
Tendency to split: Slight or absent.
Sides: Equal.
Surface: Pitted toward apex, less pitted toward the base.
Use: Fresh market and ice cream production.
Keeping quality: Excellent.
Shipping quality: Excellent.

I claim:

1. A new and distinct variety of white peach tree, substantially as illustrated and described herein, particularly characterized by a medium vigorous growth, late clinging ripening, having white flesh color, the skin deep red color located on a side facing the sun with the flesh firm and having a full flavor and large juice content.

* * * * *

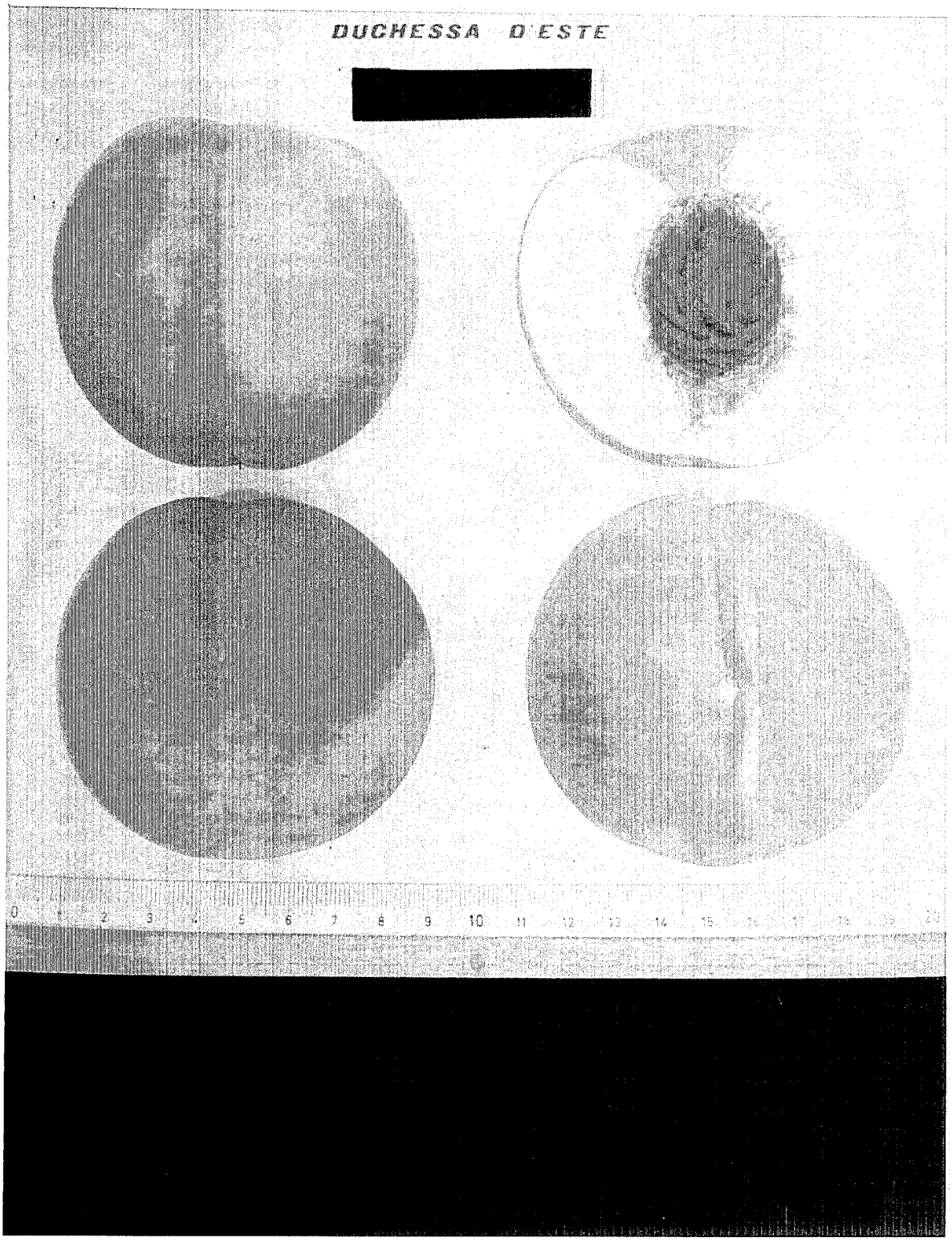
DUCHESSA D'ESTE
[redacted]
0 1 2 3 4 5 6 7 8 9 10 11 12 13 14 15 16 17 18 19 20
[redacted]

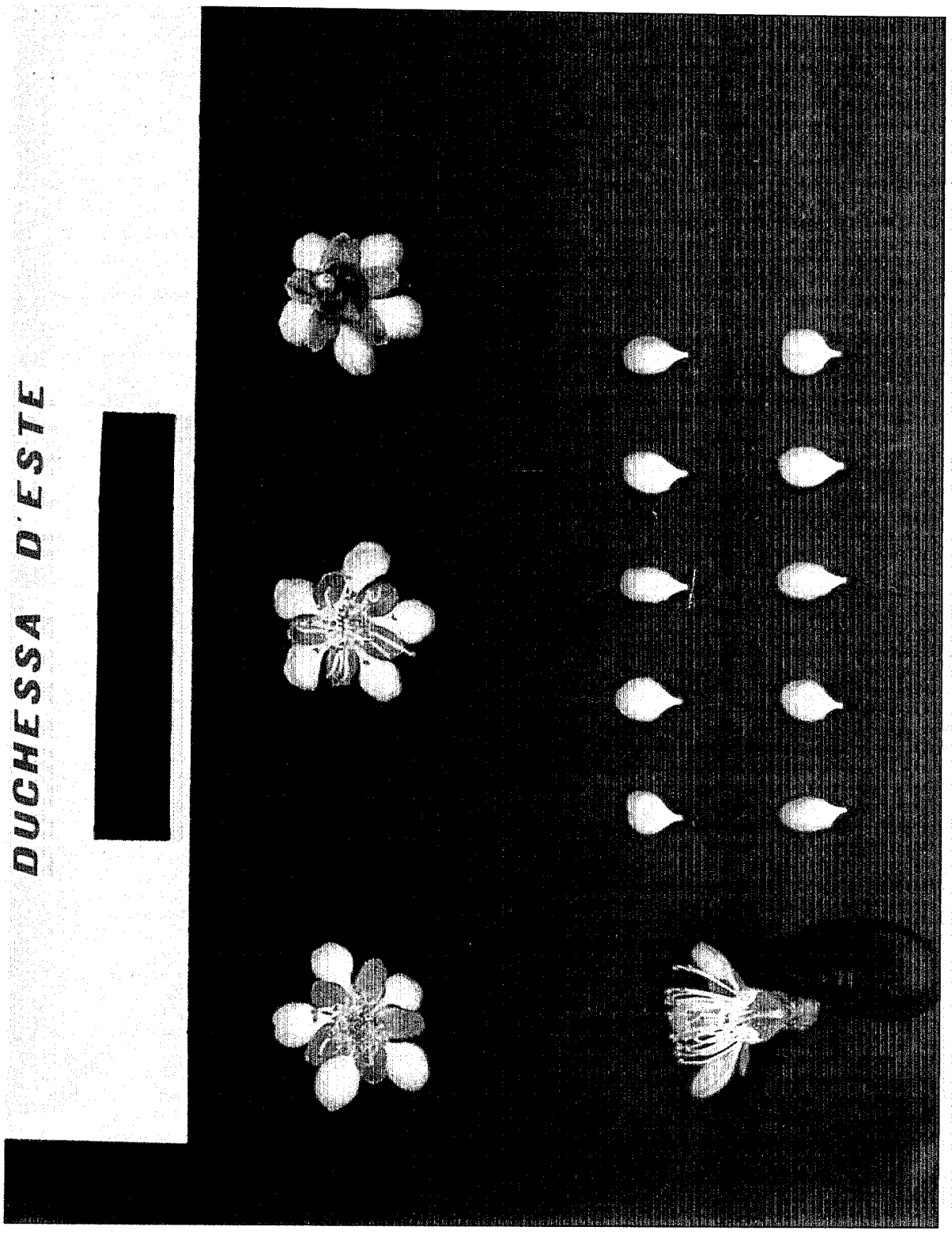
DUCHESSA D'ESTE

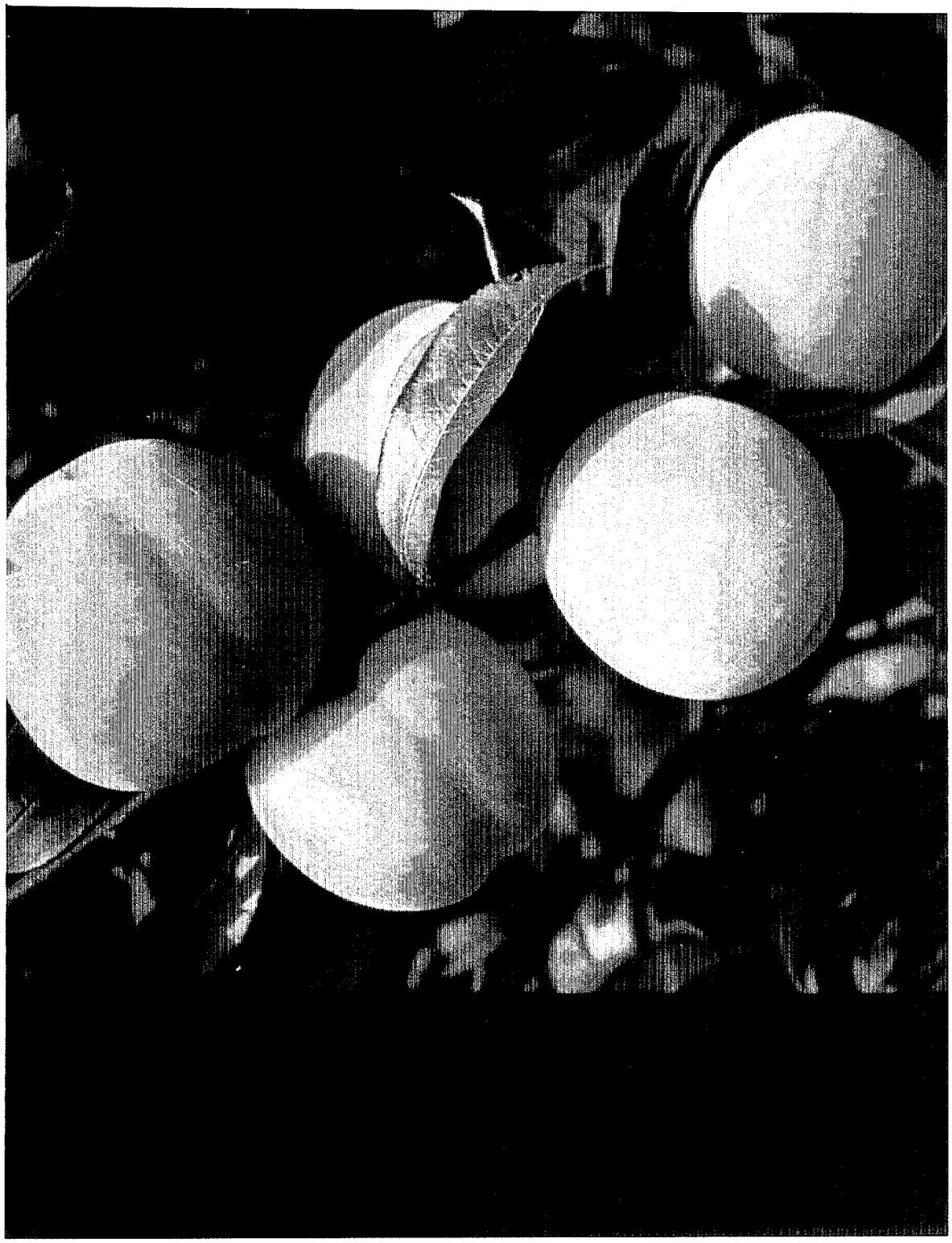

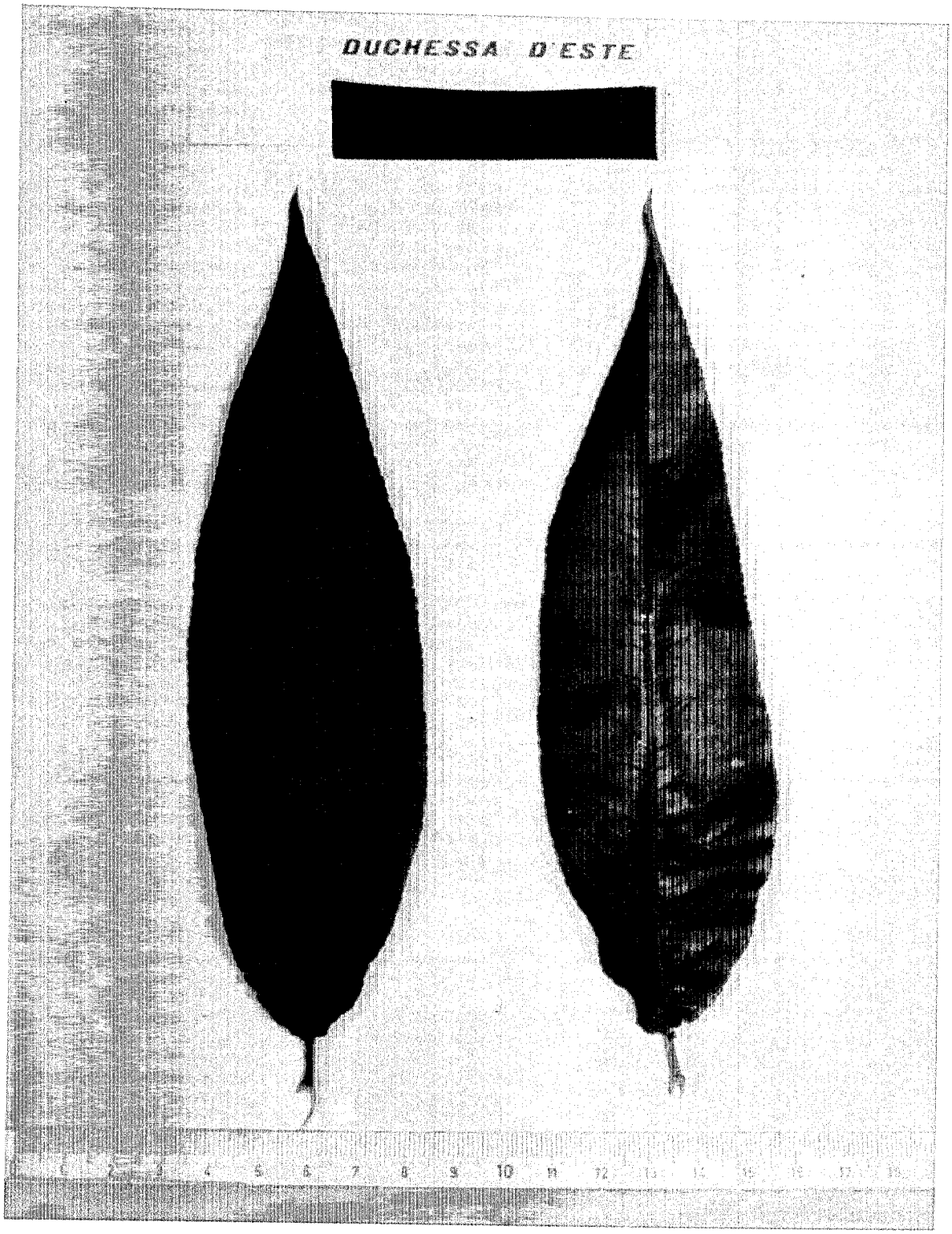
DUCHESSA D'ESTE
[redacted]